United States Patent [19]

Day

[11] 4,232,688
[45] Nov. 11, 1980

[54] DENTAL GINGIVAL RETRACTION CORD DISPENSER

[75] Inventor: Reed H. Day, Bothell, Wash.

[73] Assignee: Pascal Company, Inc., Bellevue, Wash.

[21] Appl. No.: 945,830

[22] Filed: Sep. 26, 1978

[51] Int. Cl.³ .................................................. A61C 15/00
[52] U.S. Cl. ............................................................ 132/91
[58] Field of Search .................................... 132/89–92; 222/534; 242/141, 146

[56] References Cited

U.S. PATENT DOCUMENTS

| | | | |
|---|---|---|---|
| 1,955,428 | 4/1934 | Ladwig | 132/92 R |
| 3,490,659 | 1/1970 | Vange et al. | 222/534 |
| 3,851,805 | 12/1974 | Hazard | 222/534 |

Primary Examiner—G. E. McNeill
Attorney, Agent, or Firm—Gregory W. Moravan; Roy E. Mattern, Jr.; David H. Deits

[57] ABSTRACT

A gingival cord container cap is disclosed featuring a cord dispensing gate mechanism formed by cooperating parts of a pivoted dispensing spout and a cap base in which the spout is socketed. Cord threaded out of the container through a hole in the cap base and through the spout may be withdrawn freely when the spout is swung into alignment with the hole in the base (i.e., the gate-open position). As the spout is pivoted out of such alignment (closing the gate) the cord is pinched and held, so that it may be cut off flush with the aperture of the spout, protectively retaining the remainder in the container. Swinging the spout back into aligned position causes a short segment of the pinched cord to be automatically projected out of the tip of the spout where it can be manually grasped for withdrawing additional cord from the container as needed.

10 Claims, 5 Drawing Figures

DENTAL GINGIVAL RETRACTION CORD DISPENSER

BACKGROUND OF THE INVENTION

This invention relates to improvements in dispensing cord containers; more specifically, to a dispensing cap for gingival cord containers. While disclosed in its preferred embodiment for that application in the dental profession, it will be recognized that features of the invention are also of utility in other fields of use.

The use of gingival retraction cord in the dental profession typically involves frequent dispensing of short lengths of cord from a roll or other bulk source of cord. The high standards of hygiene employed by the profession make it desirable that the cord be protected from contamination at all times. It is therefore desirable that the cord supply for use be stored entirely within a closed, antiseptic container. During times of withdrawal of the cord when lengths to be severed for use are required, it is desirable that the cord be exposed to as little manual handling as possible. Thus, the requirements of the profession dictate a retraction cord dispensing device in which cord may be stored in a sterile environment and dispensed in any desired length with a minimum of exposure to contamination.

The demands of the profession also make it desirable that a dentist or his assistant be able to quickly and efficiently obtain any desired length of retraction cord from the stored coil. Any delay caused by having to untangle the cord or thread it through a dispenser, or by awkward handling requirements in withdrawing and severing the required lengths is highly undesirable in view of the critical time constraints and immediacy of demands during treatment of a patient.

The practice within the dental profession in the past has been to store retraction cord in narrow-mouthed plastic bottles with screw caps. Typically, the cord is not rolled or coiled within the bottle, resulting in occasional tangling of the cord and attendant inefficiency in use. Also, since there is no positive means for grasping the cord when the cap is off the bottle, the end of the cord occasionally falls back into the bottle where it can be manually extracted only with some difficulty. To guard against this, the common practice has been to leave a short length of cord exposed outside the bottle and grasped by the screw cap. This practice, however, it unsightly and exposes the end of the cord to contamination.

Therefore, a basic object and purpose of this invention is to provide a device which stores the retraction cord in a protected environment when not in use.

A further object of this invention is to provide a device which facilitates quick and reliable dispensation of any desired length of retraction cord.

It is a further object of this invention to provide a cord dispensing container cap incorporating a gate device, closure of which holds the cord firmly to facilitate severing the withdrawn length at the tip of the dispensing spout and thereafter continues to hold the severed retained end of the cord against falling back into the container or slipping father out of the spout.

It is a further object of this invention to provide a cord dispensing gate device, the opening of which simultaneously both releases the cord for withdrawal from the container and projects the retained end of the cord sufficiently beyond the tip of the dispensing spout to allow it to be grasped readily for withdrawl of additional cord from the container.

SUMMARY OF THE INVENTION

With the foregoing and related objectives in view, the invention utilizes in novel manner a type of dispensing cap device heretofore used on containers of skin lotions and other liquids. The cooperating socket surfaces of the cap's dispensing spout that serve as a valve device, opened and closed by swinging of the spout into and out of alignment with a hole in the cap base, here serve in a unique functional relationship with gingival retraction cord, threaded through the hole and spout, to act as a cord dispensing gate. With its inner end or hub of enlarged semicylindrical form and socketed in a complementary formed recess in the cap base to pivot about a transverse axis, the cord dispensing spout serves as a handle to open and close the dispensing gate by swinging into and out of alignment with the cap base hole.

When the spout is pivoted out of alignment with the cap base hole, the cord is pinched and held against withdrawal from the container between the semicylindrical end surface of the spout and an opposing ridge on the cap socket wall in the form of a raised annular lip around the hole in the cap base. In that position of the spout, the cord can be conveniently severed close to the tip of the spout. The remaining cord will be held securely against falling back into the container. Moreover the remaining cord extends from the spout tip back to the hole in the cap by a circuitous route including a partial wrap around the semicylindrical socket portion of the spout. The several elements cooperate in unique manner such that when the spout is swung back toward aligned position, a short but readily graspable length of cord is projected automatically out of the tip of the spout and the pinching grip on the cord is released so as to permit withdrawing additional cord from the container. The elements cooperating for that purpose include: the availability of the length of cord embodied in that partial wrap, the free slidability of the end portion of cord in the spout bore and the pinching, sliding feed action of the aforementioned ridge on the cap socket wall.

The cord dispenser is particularly useful with a helically wound, self-supporting coil of cord which is dispensed from the center of the coil. Cord packaged in this manner is self-supporting until entirely consumed and does not require bobbins or spools. Dispensing the cord from the center of the coil virtually eliminates inteference of coil turns which may otherwise cause tangling during cord withdrawal.

DESCRIPTION OF THE PREFERRED EMBODIMENT

Figure 2:
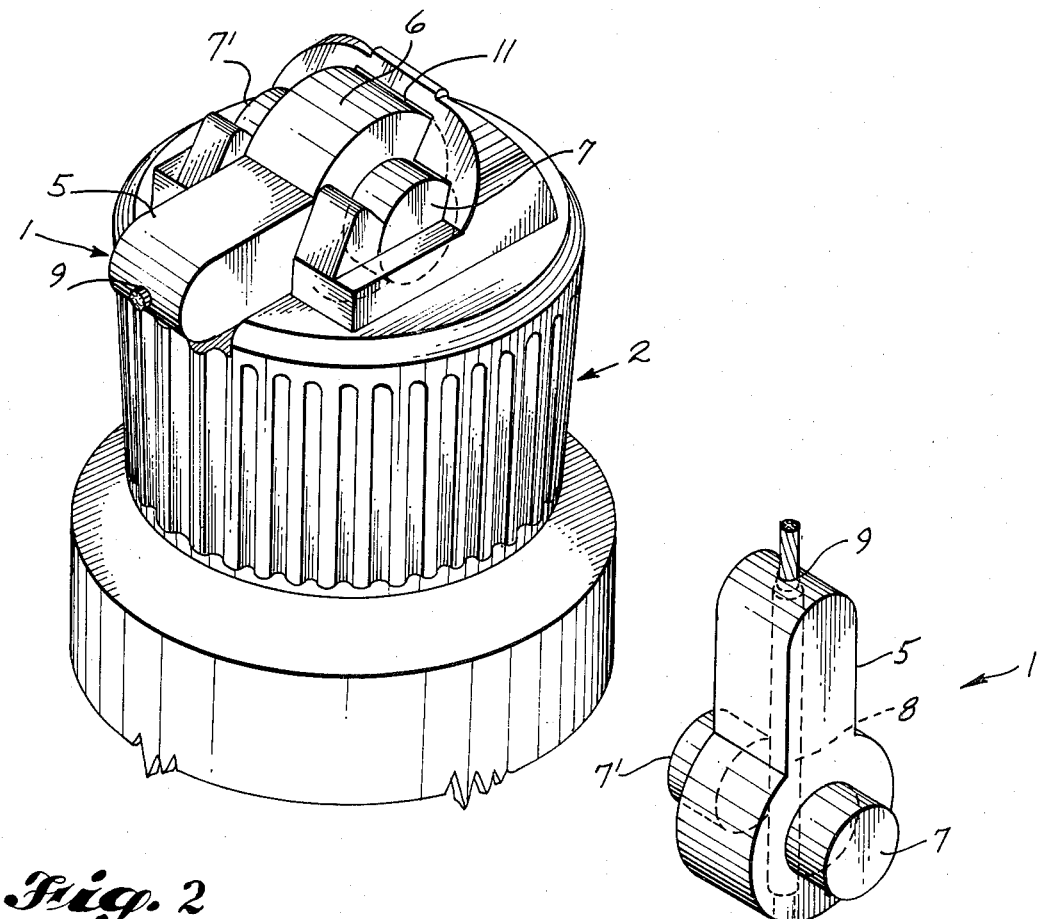
FIG. 2 is a perspective view of the cord dispenser in its closed, cord-holding position.

Referring to FIGS. 1-5, inclusive, the illustrative and preferred embodiment of the cord dispenser comprises a dispensing spout 1 pivotally mounted on a base 2 in the form of a threaded container cap. The leading end of cord 3 stored coiled at 15 in container 4 (such as a plastic bottle on which the cap is mounted) is threaded through a central hole 13 in the dispenser base 2 and through a central bore 8 in the dispensing spout 1.

Figure 1:
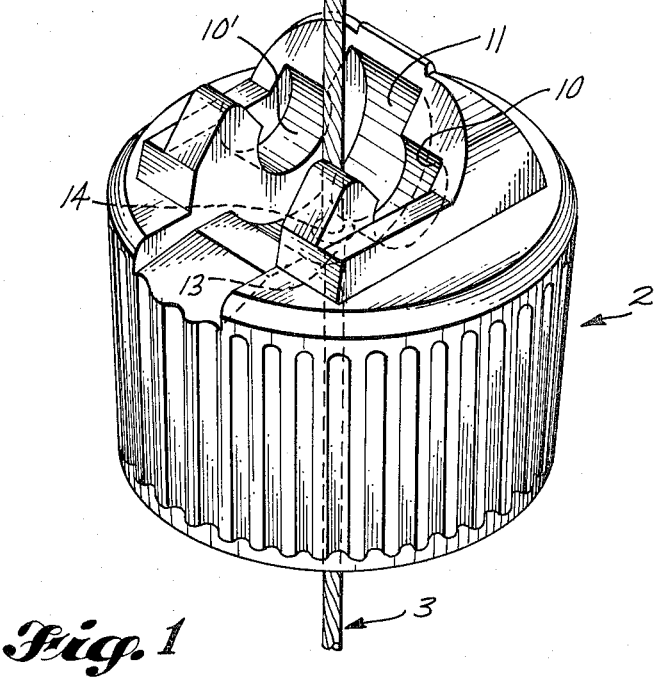
FIG. 1 is a perspective view of the preferred embodiment of the invention with the spout separated from the cap for illustration purposes and oriented in its gate-open position.

As shown in particular in FIG. 1, the device is as designed commercially for a known type of lotion dispenser cap. As such, a number of details illustrated for convenience herein are not essential nor of special purpose to the present invention. The dispensing spout 1 comprises an elongated dispensing arm 5 extending radially from a semicylindrical hub 6. Extending coaxially from each side of the hub 6 are stub shafts 7 and 7'. The cord is threaded through a straight bore 8 which passes diametrically through the center of the hub 6 and along the longitudinal axis of the dispensing arm 5. The cord emerges through an orifice 9 at the tip of the dispensing arm 5. The diameter of the orifice is or may be slightly less than the diameter of the bore 8. The orifice diameter is greater than the diameter of the cord by only so much as to allow the cord to slide freely through the aperture. Herein, the term "semi", such as in "semicylindrical", is used in its more general sense and not to denote precisely "half" of something.

As is also shown in particular in FIG. 1, the dispenser base 2 comprises aligned opposing semicylindrical stub shaft bearing sockets 10 and 10' and, in the space between them, a semicylindrical socket 11 of larger diameter accommodating the spout hub 6. Hole 13 in the base of socket 11 passes centrally through the dispenser cap base 2 and is encircled by a protruding annular lip or ridge 14 that presses slidably against the semicylindrical surface of the spout hub 6 with the parts assembled. Hole 13 and bore 8 lie in a common plane. The sockets 10 and 10' extend over somewhat more than 180 degrees so that once the stub shafts 7 and 7' are snapped into position, permitted by resilient flexibility of the base material, for example, polyethylene plastic, they will pivotally retain the shafts as depicted.

Figure 5:
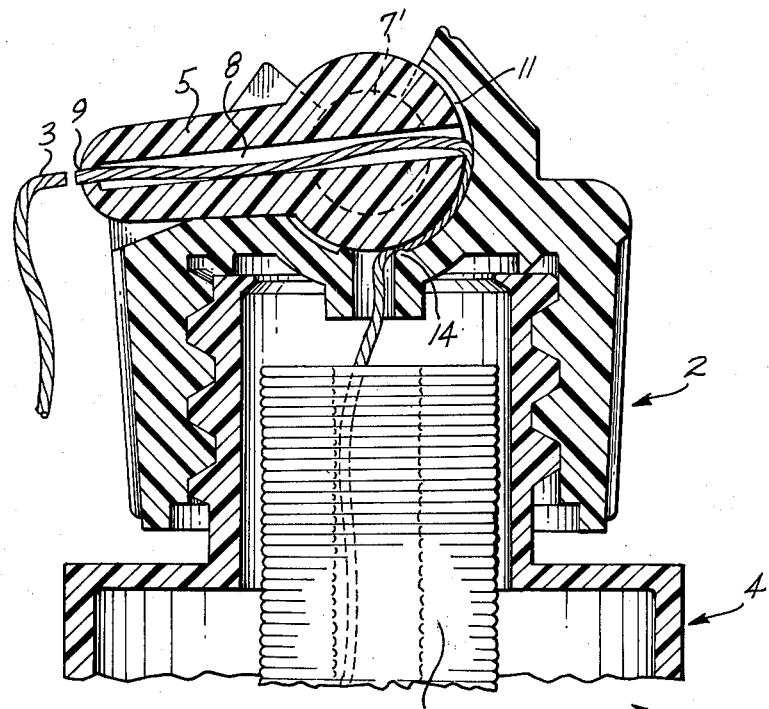
FIG. 5 is a sectional view of the cord dispenser in its closed position, the view also showing a length of cord severed at the tip of the spout.
Figure 4:
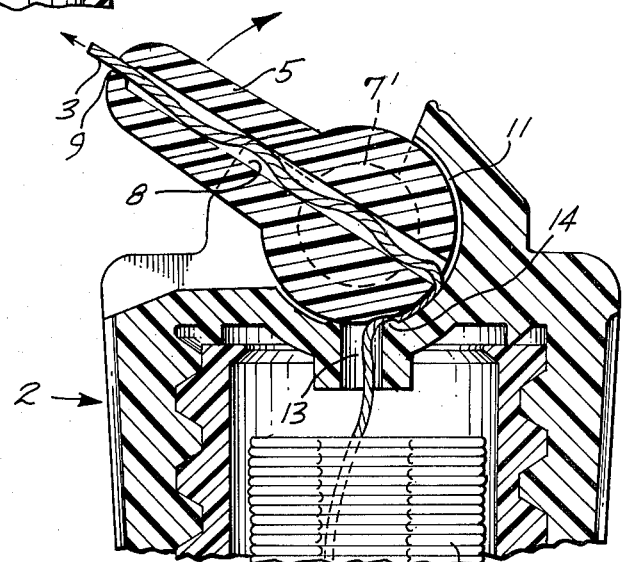
FIG. 4 is a sectional side view of the cord dispenser in the process of being opened.
Figure 3:
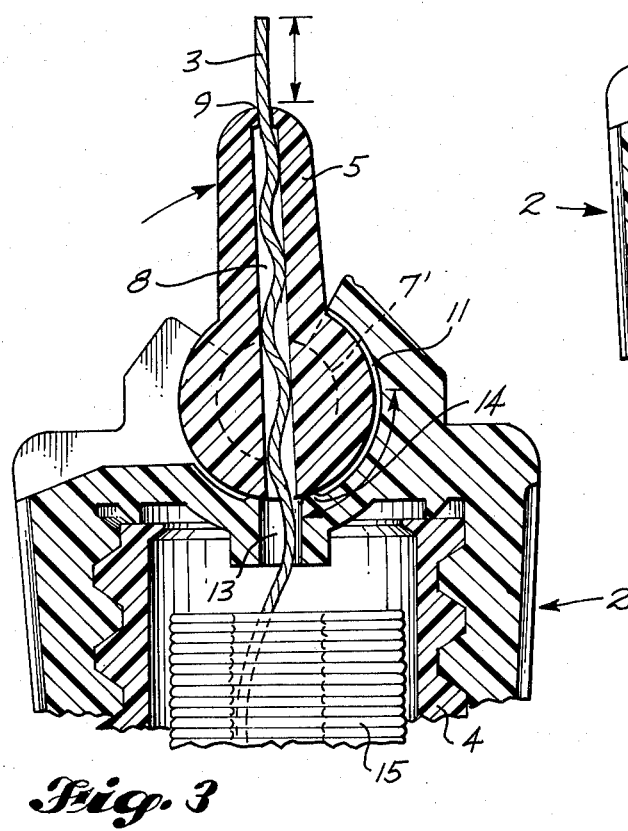
FIG. 3 is a sectional side view of the cord dispenser in its open, cord-released position.

The spout hub socket 11 is also semicylindrical and its arc circumferentially offset from the hole 13. The resultant semiannular gap between the hub surface and the surface of socket 11 slidably accommodates a partial wrap of the cord 3 extending from hole 13 to the spout bore 8 when the spout 1 is in its transversely disposed position (FIGS. 2 and 5). The pivoted spout, spout bore, spout hub cylindrical surface, base cylindrical surface, hole 13 and hole lip or ridge 14 cooperate to perform functions that can be appropriately characterized as those of a dispensing gate. Thus, with the gate closed (with the spout arm 5 disposed transverse to the axis of hole 13) the cord is pinched and held against sliding in or out of the hole 13. Thus, when the spout is being swung from aligned position into the closed, transverse position with a length of cord having previously been drawn out through bore 8, the revolving motion of the spout draws a certain amount of cord back through the bore and wraps it around the spout hub 6. During that process, pressure of the lip 14 pinching the cord slidably against the cylindrical surface of spout hub 6 exerts the holding force that permits rotation of the spout to draw the cord inwardly through bore 8. In the gate-open position, illustrated in FIGS. 1 and 3, the bore 8 of the dispensing spout 1 is aligned with the hole 13 in the cap base 2 and the pinching action of the lip 14 is terminated. Thus, cord 3 may be drawn freely from the bottle 4 through the dispenser. Thereafter, upon swinging of the spout into its transverse, closed position the cord 3 is securely held so that it may be cut off substantially flush with the orifice 9 by a scalpel or knife applied at the tip of the dispensing arm 5. Moreover, the severed retained end of the cord continues to be pinched and held by the lip 14, so that it cannot slide back into the container 4. During subsequent pivoting of the spout 1 from the transverse closed position (FIGS. 4 and 5) aligned open positions (FIG. 3), the cord 3, being pinched in sliding contact with the surface of spout hub 6, is pushed, progressively out of the spout bore 8 until the bore aligns with the opening 13. At that point a sufficient amount of cord projects from the spout orifice to be readily grasped, and since it is also released from the grip of lip 14, any desired amount of cord may be drawn freely from container 4.

The length of the cord 3 partially wrapped around hub 6 when the spout lies in the closed position is determined by the hub diameter and the 90 degree swing of the spout between positions so as to project a convenient length of cord automatically from the spout each time the dispenser is opened.

The cord 3 is preferably stored as a self-supporting multilayer helical coil at 15 in the cord container 4. When being drawn from the container, the cord 3 is unwound from the interior of the coil 15. This minimizes the off-axis angle of departure of the cord from the coil in moving to the hole 13 in the dispenser base 2 and hence minimizes any tangling tendency of the coil turns.

The embodiments of the invention in which an exclusive property or privilege is claimed are defined by the following:

1. A cord dispensing device comprising:
a first cord dispensing means defining a first cord passage passing completely therethrough, said first cord dispensing means having a curved surface portion;
a second cord dispensing means defining a second cord passage passing completely therethrough, wherein said first and second cord dispensing means are held in a movable relation with respect to each other; and
a cord threaded through said first and second cord passages; wherein said second cord dispensing means includes ridge means for pinching said cord against said curved surface portion of the first cord dispensing means when said first and second cord passages are nonaligned, to prevent inadvertant retraction of said cord through said second cord passage and to hold said cord so that it may be conveniently cut after being dispensed from said cord dispensing device; said ridge means also being for preventing said cord from moving substantially in an axial direction relative to said second cord passage when said first and second cord passages are moved towards alignment to thereby automatically dispense a length of said cord from said first cord passage as said passages are moved towards alignment.

2. The device as in claim 1, wherein said ridge means comprises a lip adjacent to and at least partially surrounding one end of said second cord passage.

3. The device as in claims 1 or 2, wherein:

said first cord dispensing means comprises an elongated dispensing arm defining said first cord passage and having at one end a pivotal hub that defines said curved surface portion and has a pivot axis generally transverse to said first cord passage; and said second cord dispensing means defines a socket pivotally receiving said hub, wherein said second cord passage is located in the plane of pivotal movement of said dispensing arm.

4. The device as in claim 3, further comprising a pair of stub shafts extending coaxially from opposite sides of said hub, and wherein said second cord dispensing means define a pair of stub shaft receiving sockets which pivotally receive said stub shafts.

5. A process for a new use for a dispenser of the type comprising:

a first dispensing means defining a first passage passing completely therethrough, said first dispensing means having a curved surface portion;

a second dispensing means defining a second passage passing completely therethrough, wherein said first and second dispensing means are held in a movable relation with respect to each other; and wherein said second dispensing means includes ridge means opposing said curved surface at least some of the time when said passages are nonaligned; and wherein the method comprises the step of positioning a cord in said passages.

6. The process of claim 5, further comprising the steps of:

pinching said cord between said ridge means and said curved surface of the first dispensing means; and positioning said cord between at least a portion of said curved surface and at least a portion of said second dispensing means.

7. The process of claims 5 or 6, wherein said ridge means comprises a lip adjacent to and at least partially surrounding one end of said second passage.

8. The process of claims 5 or 6, wherein said first dispensing means comprises an elongated dispensing arm defining said first passage and having at one end a pivotal hub that defines said curved surface portion and has a pivot axis transverse to said first passage; and said second dispensing means defining a socket pivotally receiving said hub, wherein said second passage is located in the plane of pivotal movement of said dispensing arm.

9. The process of claim 8, wherein said ridge means comprises a lip adjacent to and at least partially surrounding one end of said second passage.

10. The process of claim 9, wherein said pivotal hub further comprises a pair of stub shafts extending coaxially from opposite sides of said hub, and said second dispensing means defines a pair of stub shaft receiving sockets which pivotaly receive said stub shafts.

* * * * *